United States Patent [19]

Anderson

[11] Plant 4,435

[45] Jul. 10, 1979

[54] NECTARINE TREE (43-G-587)

[75] Inventor: Frederic W. Anderson, Merced, Calif.

[73] Assignee: Reedley Nursery, Inc., Reedley, Calif.

[21] Appl. No.: 934,542

[22] Filed: Aug. 17, 1978

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine which is large, vigorous, spreading, foliated with medium size, ovate, acutely pointed leaves having a crenate margin and alternate, medium size, reniform glands, blooms mid-season with large, pink flowers, and is a regular and very productive bearer of early June ripening, medium size, uniform, symmetrical, globose, freestone fruit having yellow skin substantially overspread with red, and yellow flesh.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program; such variety being embraced by Class 41, Plants, of the U.S. Patent Office MANUAL OF CLASSIFICATION.

2. Prior Varieties

Among the existent varieties of nectarine trees which are known to me, I make particular reference to the Red Diamond (U.S. Plant Pat. No. 3,165), Early Sun Grand (U.S. Plant Pat. No. 1,420), Aurelio Grand (U.S. Plant Pat. No. 3,755), and May Grand (U.S. Plant Pat. No. 2,794)—all as mentioned hereinafter in this specification.

ORIGIN OF THE VARIETY

The present variety of nectarine tree was originated by me, in my experimental nursery and orchard located as aforesaid, as a first generation cross between the Red Diamond nectarine and the Early Sun Grand nectarine. In maturity, such cross evidenced desirable characteristics for commercial production, and I, therefore, selected it for asexual reproduction.

ASEXUAL REPRODUCTION OF THE VARIETY

Subsequent to origination and selection by me of the present variety of nectarine tree, I asexually reproduced it by top-working on mature trees in my said experimental orchard, and—in maturity—such reproductions ran true to the original tree in all respects.

SUMMARY OF THE VARIETY

The herein-claimed new and distinct variety of nectarine tree is large, vigorous, spreading, foliated with medium size, ovate, acutely pointed leaves having a crenate margin and alternate, medium size, reniform glands, blooms mid-season with large, pink flowers, and is a regular and very productive bearer of early June ripening, medium size, uniform, symmetrical, globose, freestone fruit having yellow skin substantially overspread with red, and yellow flesh.

The variety is further characterized by fruit having a ripening period between the Aurelio Grand and May Grand nectarines, and thus is available to an intermediate market; the fruit being of a firmness which permits of long distance shipping and provides a substantial shelf life.

BRIEF DESCRIPTION OF THE DRAWING

The drawing is an illustration, by photographic reproduction in color, of a twig with leaves, and separate fruit; one of the latter being partially cut away to expose the flesh and the stone.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Production.*—Very productive.
- *Bearing.*—Regular bearer.

Trunk:
- *Size.*—Medium.
- *Texture.*—Medium.

Branches:
- *Size.*—Stocky to medium.

Leaves:
- *Size.*—Medium. Average length — 5½". Average width — 1½".
- *Form.*—Ovate. Acutely pointed.
- *Thickness.*—Medium.
- *Texture.*—Smooth.
- *Margin.*—Crenate.
- *Petiole.*—Medium length.
- *Glands.*—Number and position — usually 2 on petiole and 2 on base of blade. Alternate. Medium size. Reniform.
- *Color.*—Top side — Medium green (22-L-8). Under side — Lighter green (21-K-7).

Flower buds:
- *Size.*—Medium.

*Length.*—Medium.

Flowers:

*Blooming period.*—Date of first bloom—Mar. 3, 1978. Date of full bloom — Mar. 14, 1978. Medium, as compared with other varieties.

*Size.*—Large.

*Color.*—Pink.

Fruit:

*Maturity when described.*—Hard.

*Date of first picking.*—June 3, 1978.

*Date of last picking.*—June 12, 1978.

*Size.*—Uniform. Medium. Average diameter axially — 2⅜". Average transversely in suture plane 2⅜".

*Form.*—Uniform. Symmetrical. Globose.

*Suture.*—A shallow, inconspicuous line with slight depression beyond pistil point.

*Ventral surface.*—Rounded slightly.

*Cavity.*—Average depth — ⅜". Average breadth — 7/16".

*Base.*—Rounded to truncate.

*Apex.*—Short. Rounded. Inconspicuous.

Skin:

*Thickness.*—Medium.

*Texture.*—Medium.

*Tendency to crack.*—Slight.

*Down.*—Wanting.

*Color.*—Yellow (9-L-5) substantially overspread with red (5-L-6) shading to darker red (7-L-6).

Flesh:

*Juice.*—Moderate.

*Texture.*—Firm. Crisp. Melting.

*Fibers.*—Few. Fine.

*Ripens.*—Evenly.

*Flavor.*—Subacid. Delicate.

*Eating quality.*—Good to best.

Stone:

*Type.*—Free.

*Size.*—Medium. Average length — 1½". Average breadth — 1". Average thickness — ⅝".

*Form.*—Oblong.

*Base.*—Straight.

*Apex.*—Rounded to acute.

*Sides.*—Equal.

*Ridges.*—Rounded.

*Pits.*—Elongated.

*Ventral edge.*—Thick.

*Dorsal edge.*—Full.

*Tendency to split.*—None noted.

*Color.*—Beige (13-H-7).

Use: Market. Dessert. Long distance shipping.

Keeping quality: Good.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized by fruit having a ripening period between the Aurelio Grand and May Grand; the fruit being of a firmness which permits long distance shipping and provides a substantial shelf life.

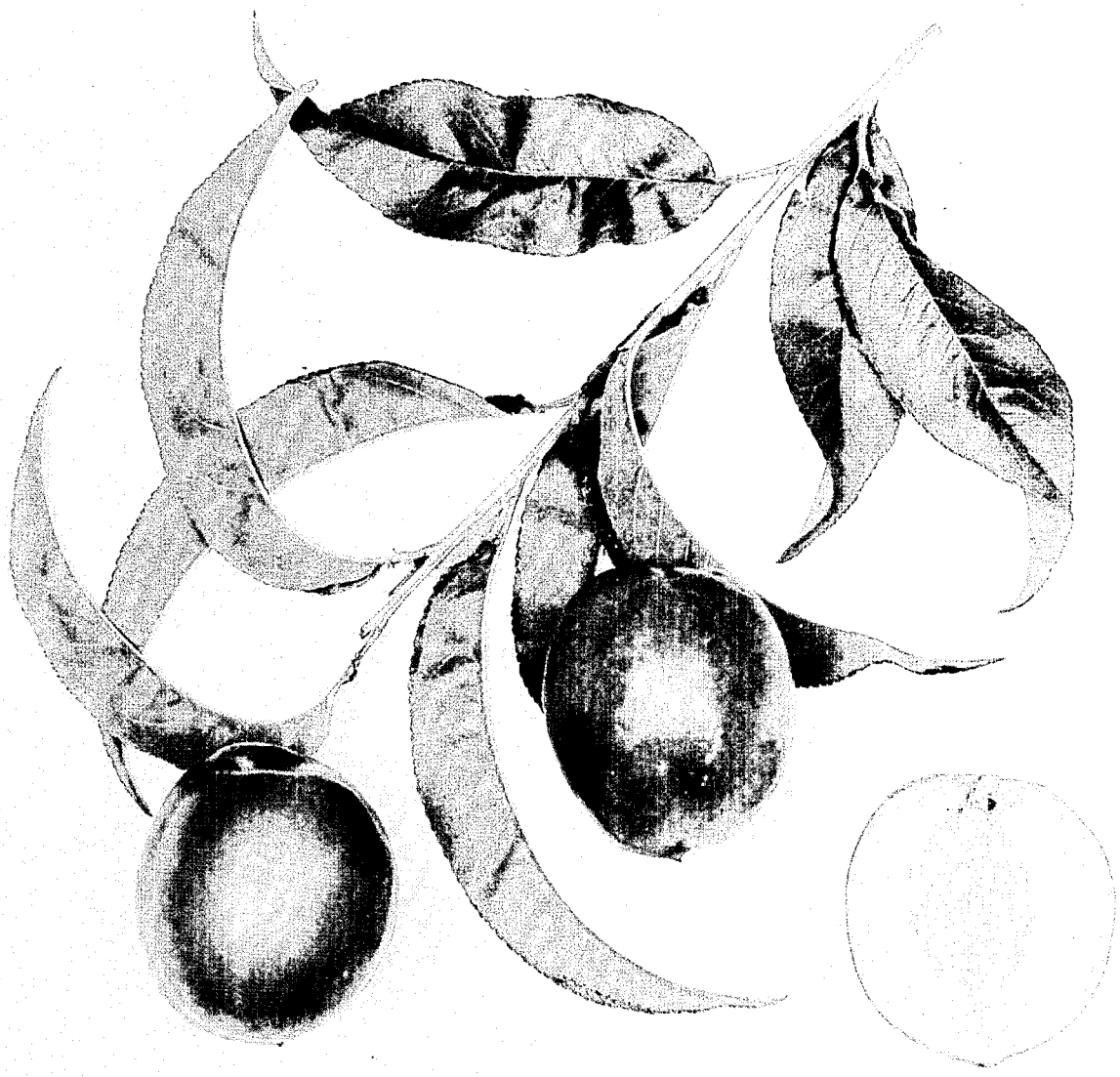

* * * * *